United States Patent
Yamashita

[11] Patent Number: 5,956,565
[45] Date of Patent: Sep. 21, 1999

[54] ANALYSIS APPARATUS AND ANALYSIS METHODS FOR SEMICONDUCTOR DEVICES

[75] Inventor: Hiroshi Yamashita, Takatsuki, Japan

[73] Assignee: Matsushita Electronics Corporation, Japan

[21] Appl. No.: 08/748,655

[22] Filed: Nov. 14, 1996

[51] Int. Cl.$^6$ ................................................. H01L 21/302

[52] U.S. Cl. ........................... 438/14; 438/712; 438/716; 438/720; 438/976; 204/192.33; 204/192.34

[58] Field of Search ................................ 438/14, 17, 976, 438/712, 734, 716, 720; 204/192.32, 192.33, 192.34

[56] References Cited

U.S. PATENT DOCUMENTS

| | | | |
|---|---|---|---|
| 4,278,493 | 7/1981 | Petvai | 156/643 |
| 5,382,342 | 1/1995 | Bionta et al. | 204/192.26 |
| 5,420,796 | 5/1995 | Weling et al. | 364/468 |
| 5,447,614 | 9/1995 | Hamamura et al. | 216/192.33 |
| 5,476,006 | 12/1995 | Fujii et al. | 73/105 |
| 5,520,769 | 5/1996 | Barrett et al. | 156/626.1 |
| 5,541,411 | 7/1996 | Lindquist et al. | 250/309 |
| 5,616,921 | 4/1997 | Talbot et al. | 250/307 |

FOREIGN PATENT DOCUMENTS 2-59643  2/1990  Japan .
4-116843  4/1992  Japan .

OTHER PUBLICATIONS

Prohaska, T. et al, "In Situ Investigation of Aluminum Gallium Arsenide/Gallium Arsenide Multilayer Structures under Inert and Reactive Media by Atomic Force Microscopy" Anal. Chem. vol. 67, No. 9, pp. 1530–1535, May 1, 1995.

Friedbacher, G. et al "Investigation of Aluminum Gallium Arsenide/Gallium Arsenice Superlattices by Atomic Force Microscopy" Anal. Chem. vol. 64, No. 17, pp. 1760–1762, Sep. 1, 1992.

Primary Examiner—Bruce Breneman
Assistant Examiner—Anita Alanko
Attorney, Agent, or Firm—Parkhurst & Wendel, L.L.P.

[57] ABSTRACT

This invention aims to facilitate observation and structural analysis of crystal grains of aluminum wiring. In the process, a protective film of a semiconductor device is removed by dry etching. Next, said semiconductor device is inclined and rotated and an aluminum alloy film or laminated aluminum alloy film of the semiconductor device is scanned with a focused ion beam. Then, said aluminum alloy film or laminated aluminum alloy film is scanned with a cantilever, atomic force between said aluminum alloy film or laminated aluminum alloy film and the cantilever is measured, and the surface of said aluminum alloy film or laminated aluminum alloy film is observed in vacuum.

11 Claims, 10 Drawing Sheets

ANALYSIS APPARATUS AND ANALYSIS METHODS FOR SEMICONDUCTOR DEVICES

FIELD OF THE INVENTION

This invention relates to an analysis apparatus and analysis methods for observation and structural analysis of crystal grains in aluminum (hereinafter referred to as "Al") and Al alloy wiring in semiconductor devices.

BACKGROUND OF THE INVENTION

In general, Al atoms in Al and Al alloy wiring used for semiconductor devices migrate too easily even at relatively low temperatures as in the range of 100 to 200° C., because the melting point of Al is low. Therefore, when electric current flows in Al and Al alloy wiring, electro-migration and stress migration because of thermal stress loading occur. This causes a breaking of the wire. That is one of the major factors which lowers the reliability of semiconductor devices.

Therefore, various means of evaluation have been developed to solve the shortfalls of this migration. For example, a scanning ion microscope (hereinafter referred to as "SIM") and a transmission electron microscope (hereinafter referred to as "TEM") are being used for observation and structural analysis of crystal grains in Al and Al alloy wiring.

However, in the case of the TEM, a great amount of time and labor are required to make samples. In addition, with semiconductor devices having become more minute and highly integrated, Al wiring has become laminated and making the samples has become more difficult. In the case of the SIM, since the SIM scans ions with a large atomic radius, the resolution of images obtained is not very high and observation of minute crystal grains in Al wiring has been difficult.

DISCLOSURE OF THE INVENTION

This invention aims to solve the problems of the conventional methods and to provide an analysis apparatus and analysis methods to facilitate observation and structural analysis of crystal grains in an Al or Al alloy film that constitutes the wiring of a semiconductor device.

To accomplish this, the analysis apparatus for semiconductor devices of the invention comprises:
 a focused ion beam source for generating a primary beam to scan any areas of semiconductor devices;
 a photomultiplier for detecting secondary electrons generated by said semiconductor devices while the semiconductor devices are scanned with said primary beam;
 a nozzle for introducing etching gas; and
 a device for measuring atomic force in vacuum.

The analysis apparatus for semiconductor devices of the invention, with said construction, can easily identify crystal grains with a single beam alone and allow close observation of grain boundaries on the surface of an Al alloy film that are inhibited from oxidation.

The analysis apparatus for semiconductor devices of the invention according to another embodiment comprises a sample drive unit to incline and rotate semiconductor devices.

The analysis method for semiconductor devices according to a first aspect the invention comprises the steps of:
 removing a protective film from a semiconductor device by dry etching;
 scanning an aluminum alloy film or laminated aluminum alloy film of said semiconductor device with a focused ion beam; and
 scanning said aluminum alloy film or laminated aluminum alloy film with a cantilever, measuring atomic force between said aluminum alloy film or laminated aluminum alloy film and the cantilever, and observing the surface of said aluminum alloy film or laminated aluminum alloy film in vacuum.

With this construction, the analysis method for semiconductor devices can easily observe crystal grains in the Al alloy or laminated Al alloy film. This is realized by carrying out sputter-etching over the Al alloy or laminated Al alloy film in semiconductor devices with a focused ion beam and detecting unevenness in each crystal grain with an atomic force microscope (hereinafter referred to as "AFM"). In addition, since measurements are carried out by AFM in vacuum, oxidation of the surface of the Al alloy film is inhibited and the resolution of the image is improved.

Furthermore, with this construction, the crystal wiring information in the flat direction can be visually evaluated correctly in two dimensions. From this we can expect that the mechanism of a bad migration will be solved and also that the causes of failures can be quickly realized in manufacturing processes or development processes of semiconductor devices. This will contribute to yield stability and more rapid development of semiconductor devices.

According to a second aspect of the analysis method of the invention, in the step of scanning the aluminum alloy film or laminated aluminum alloy film of said semiconductor devices with a focused ion beam, said semiconductor devices are scanned with a focused ion beam while being inclined and rotated.

By doing this the invention carries out sputter-etching by inclining and rotating the semiconductor devices. The inhibition of the channeling effect and the crystal surface azimuth effect are emphasized, resulting in the structural analysis of the crystal grains.

A third aspect of the analysis method of the invention comprises the steps of:
 cleaving semiconductor devices;
 etching cleaved local areas of said semiconductor devices by scanning and irradiating the areas with a focused ion beam; and
 scanning the local areas of said semiconductor devices with a cantilever, measuring the atomic force between said semiconductor devices and the cantilever, and observing the surface of said semiconductor devices and the aluminum alloy film or laminated aluminum alloy film in vacuum.

Through this, it becomes easy to observe crystal grains in the Al alloy or laminated Al alloy film on the cleaved surfaces of semiconductor devices. This is realized by carrying out sputter-etching over the cleaved surface of the Al alloy film or laminated Al alloy film in semiconductor devices with a focused ion beam, and detecting the unevenness of each crystal grain with an AFM. In addition, since measurements are carried out by an AFM in vacuum, oxidation on the surface of the Al alloy film is inhibited and the resolution of the image is improved.

Because data on sectional-directional crystals of the wiring can be correctly visually evaluated in two dimensions, the invention reveals information on the shape of the surface (X-Y surface) in the direction of the depth (Z) of LSIs that have passed through the final process. The mechanism of the bad migration can be expected to be solved by this process. Causes of failures can be quickly realized in manufacturing processes or development processes of semiconductor devices This will contribute to yield stability and more rapid development of semiconductor devices.

A fourth aspect of the analysis method of the invention comprises the additional step of etching the cleaved local areas of said semiconductor devices by scanning the areas with a focused ion beam in an etching gas atmosphere. This is carried out after the step of etching the cleaved local areas of said semiconductor devices by scanning the areas with a focused ion beam, as in the third aspect.

According to a fourth aspect of the analysis method of the invention, gas-assisted etching, is carried out over the Al alloy or laminated Al alloy film of semiconductor devices with a focused ion beam. The etching gas detects unevenness of each crystal grain by an AFM. Hence, the crystal grains of the Al alloy or laminated Al alloy film of the semiconductor devices in a sectional direction can be easily observed.

A fifth aspect of the analysis method of the invention is intended to carry out etching by inclining and rotating semiconductor devices in the step of etching the cleaved local areas of semiconductor devices by scanning the areas with a focused ion beam, as in the third and fourth aspects.

In the fifth aspect, the device carries out sputter-etching by inclining and rotating the semiconductor devices. Therefore, improvement of the selection ratio of etching, the inhibition of the channeling effect and the crystal surface azimuth effect are emphasized. This realizes the structural analysis of crystal grains.

In accordance with a sixth aspect of the analysis method of the invention, the angle of the inclination of semiconductor devices is specified, as in the second and fifth aspects, as 15–30 degrees.

In accordance with a sixth aspect of the analysis method of the invention, the range of accelerating voltage of the focused ion beam is specified as 20 to 30 kV.

In accordance with a eighth aspect of the analysis method of the invention, the analysis method comprises a step of etching the cleaved surface of said semiconductor devices by scanning the area with a focused ion beam from the side and also a step of etching the cleaved surface of said semiconductor devices by scanning the area with a focused ion beam. This occurs in the step of etching the cleaved local areas of said semiconductor devices by scanning the area with a focused ion beam in third, fourth and fifth aspects.

By a method of the eighth aspect of the invention, the roughness of the cleaved surface can be reduced since the etching is carried out by scanning the cleaved surface of semiconductor devices with a focused ion beam laterally from the side.

According to a ninth aspect of the analysis method of the invention, $Cl_2$, $XeF_2$, $I_2$ or $ICl$ can be used as an etching gas.

DESCRIPTION OF THE EMBODIMENTS

The embodiments of the invention will be described with reference to the drawings.

Figure 1:
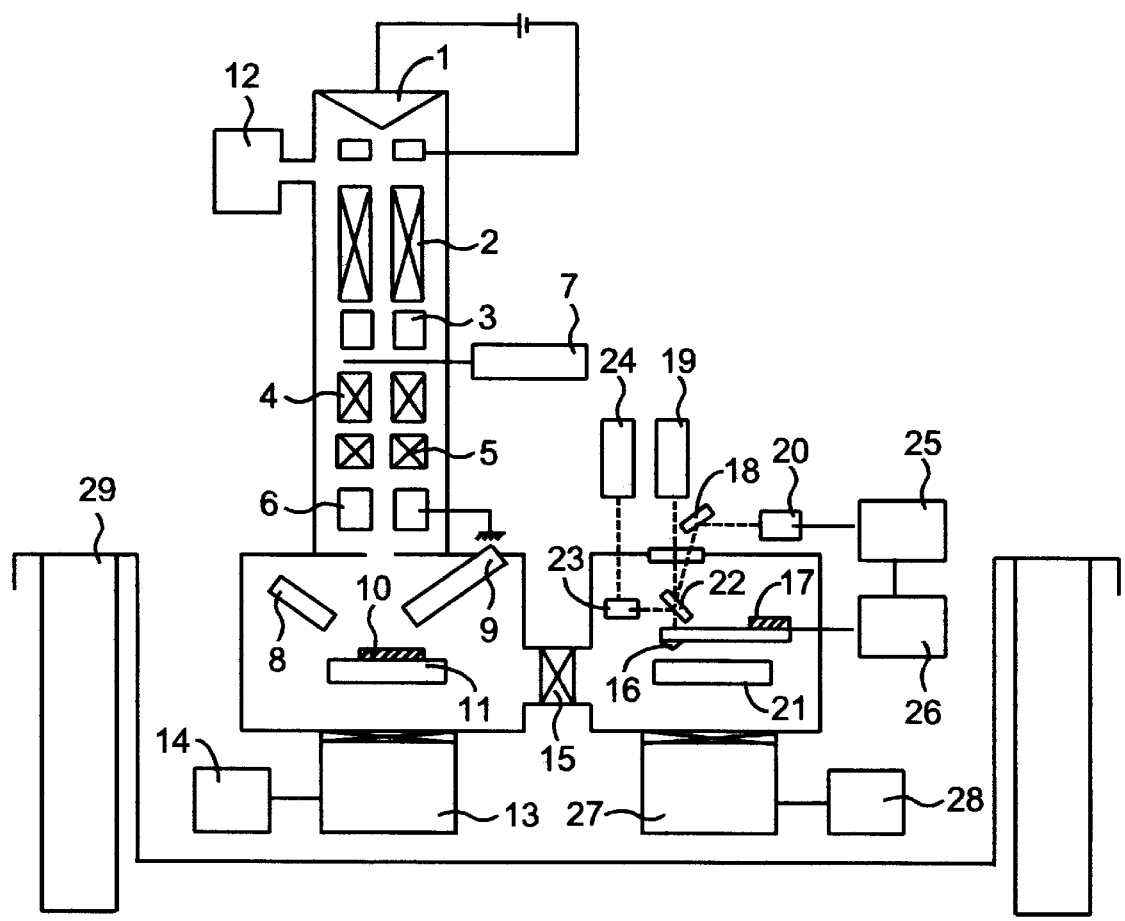
FIG. 1 is a schematic diagram of the analysis apparatus for semiconductor devices used in the first through third embodiments.

FIG. 1 is a schematic diagram of the analysis apparatus for semiconductor devices of the invention.

In FIG. 1, (1) represents a liquid metal ion source, (2) represents a condenser lens, (3) represents a blanker, (4) represents a stigmeter, (5) represents an objective lens, (6) represents a deflector, (7) represents a movable diaphragm, (8) represents a photoelectron amplifier, (9) represents a gas nozzle, (10) represents a semiconductor device, (11) represents a sample table, (12) represents an ion pump, (13) represents a turbo-molecular pump, (14) represents a rotary pump, (15) represents a gate valve, (16) represents a cantilever, (17) represents a piezo-element, (18) represents a mirror, (19) represents a laser, (20) represents a photodetector, (21) represents a sample table, (22) represents a transmission mirror, (23) represents an objective lens, (24) represents a CCD camera, (25) represents a lock-in amplifier, (26) represents a resonance-frequency generating circuit, (27) represents a turbo-molecular pump, (28) represents a rotary pump, and (29) represents an oscillation eliminating table.

Figure 2:
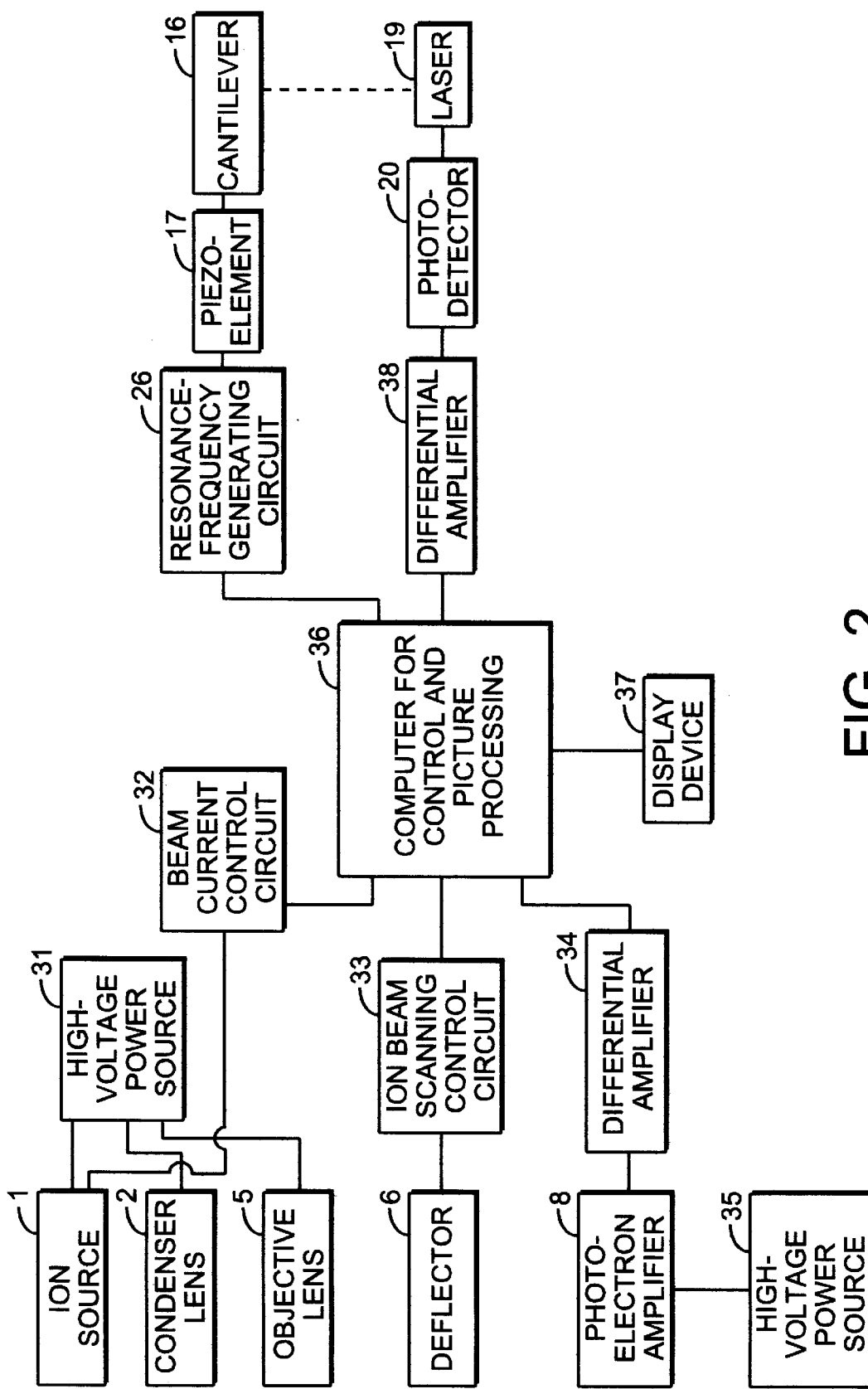
FIG. 2 is a circuit schematic diagram of the analysis apparatus for semiconductor devices used in the first through third embodiments.

FIG. 2 is a circuit schematic diagram of the analysis apparatus for semiconductor devices of the invention.

In this diagram, (1) represents an ion source, (2) represents the condenser lens, (5) represents the objective lens, (31) represents a high-voltage power source, (32) represents a beam current control circuit, (6) represents the deflector, (33) represents an ion beam scanning control circuit, (8) represents the photoelectron amplifier, (34) represents the differential amplifier, (35) represents a high-voltage power source for photoelectron amplifier, (36) represents a computer for control and picture processing, (37) represents a display device, (16) represents the cantilever, (17) represents the piezo-element, (26) represents the resonance-frequency generating circuit, (19) represents the laser, (20) represents the photodetector, and (38) represents a differential amplifier.

Next, the drawings of the analysis method for crystal grains of an Al alloy or laminated Al alloy film of the semiconductor devices of the first embodiment, using the analysis apparatus, will be described.

FIGS. 3(a)–(d) show cross-sectional views showing the steps of the analysis method for semiconductor devices of the invention.

Figure 3A:
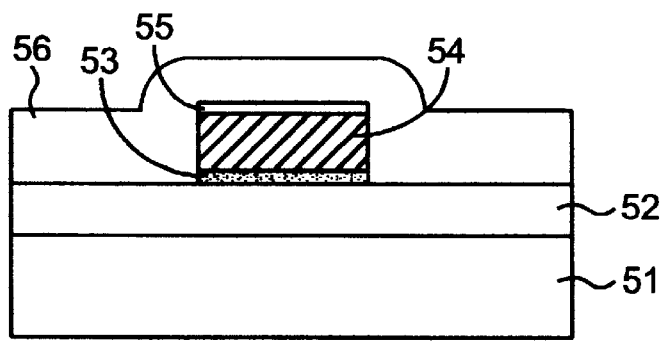
FIGS. 3(a)–3(d) show cross sectional views showing the steps of the analysis method for semiconductor devices in the first embodiment.

FIG. 3(a) shows a cross section of a laminate-structured wiring area of the semiconductor device (10). In this figure, (51) represents a silicon substrate, (52) represents an inter-level insulating film, (53) represents a barrier metal, (54) represents an Al alloy film, (55) represents a cap metal, and (56) represents a protective film.

Figure 3B:
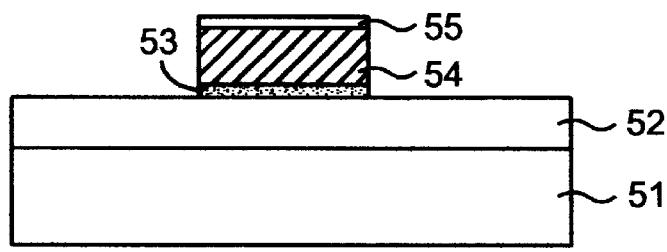

The protective film (56) of the semiconductor device (10) shown in FIG. 3(a) was removed with a dry etching device using mixed gas made of carbon tetrafluoride gas ($CF_4$) and oxygen so as to expose the cap metal (55), as shown in FIG. 3(b).

Figure 3C:
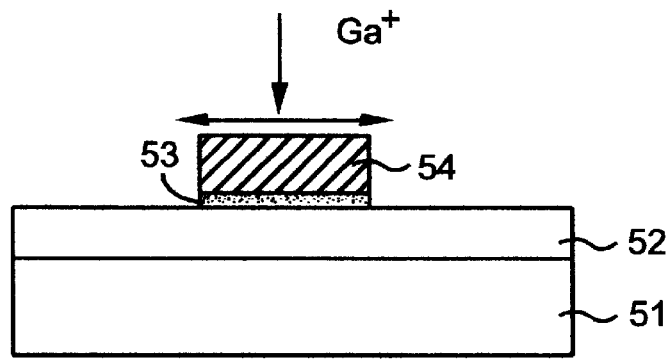

Next, the semiconductor device (10) was scanned, for example, with a positive Ga focused ion beam having a beam diameter of 0.1 μm, an ion beam current of 150 pA, and an accelerating voltage of 30 kV. Sputter-etching was carried out on the cap metal (55) to expose the Al alloy film (54), as shown in FIG. 3(c). The surface of preferred orientation, for example the Al (111) surface, was selectively etched and unevenness was formed on the Al surface.

Figure 3D:
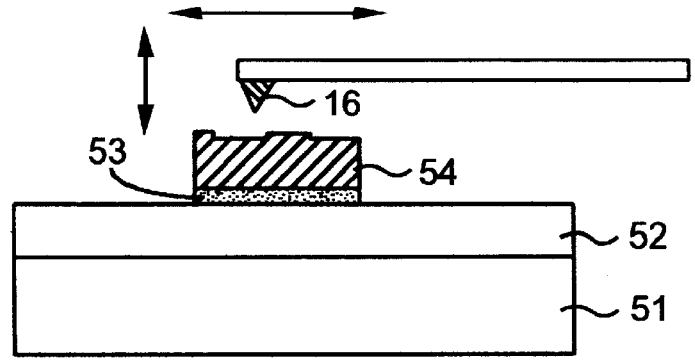

FIG. 3(d) shows a cross-section of the state of unevenness. The amount of etching was large on the Al (111) surface and small on the Al (100) surface and the Al (110) surface.

Next, as shown in FIG. 3(d), the surface of the semiconductor device (10) was scanned with the cantilever (16), using an AFM. The atomic force between the semiconductor device (10) and the cantilever (16) was measured and semiconductor device (10) was observed.

A SiN needle or SiC needle was used as a probe for the AFM. While measuring was with the AFM, the atomic force (attraction and repulsion) was kept at a constant level.

In general, sputtering yields of polycrystal bodies by ion beams greatly depend on the azimuth of the surface of the crystal grains, grain boundary, and precipitated material. Therefore, unevenness information shown by the AFM is influenced by the difference of the crystal azimuth, grain boundary, and precipitated material. In the crystal boundary, precipitation of impurities and changes of the crystal azimuth occurred. Through this, crystal grains were observed by using an AFM. An image with a high resolution was obtained by the AFM.

The spatial resolution of the AFM is determined by the radius of curvature of the tip of the cantilever (16). If the cantilever (43) is sufficiently sharp, a resolution of 0.2 nm can be obtained. In addition, insulating films, such as an oxide film and a nitride film, can be measured with the AFM. Also the shape and interface of the semiconductor device (10), as well as the wiring area of semiconductor devices, can be correctly observed. Since measurements are carried out with an AFM in vacuum, oxidation on the surface of the Al alloy film is inhibited and the resolution of the image is improved.

In the invention, a semiconductor device with a specific pattern was described. But the same effect is obtained in observation of crystal grains of the Al alloy or laminated Al alloy film that do not have a pattern.

Now, the drawing of the analysis method for crystal grains of the Al alloy or laminated Al alloy film of semiconductor devices of the second embodiment of the invention will be described. In the second embodiment, the same analysis apparatus was used as in the first embodiment.

FIGS. 4(a)–4(d) show steps of the analysis method for the semiconductor devices of the embodiment.

Figure 4A:
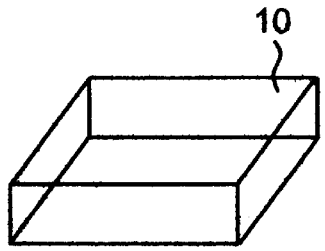
FIGS. 4(a)–4(e) show cut-away views showing steps of the analysis method for semiconductor devices in the second embodiment.
Figure 4B:
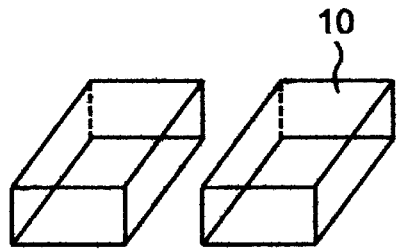
Figure 4C:
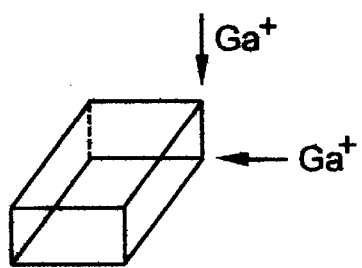
Figure 4E:
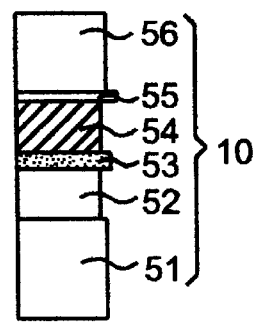

The semiconductor device (10), having a wiring area with a laminated structure shown in FIG. 4(a), was cleaved with a diamond pen or a dicing saw, as shown in FIG. 4(b). Next, as shown in FIG. 4(c), in order to reduce roughness of the cleaved surface of the semiconductor device (10), sputter-etching was carried out over the cleaved surface of said semiconductor device (10) laterally from the side by using a positive Ga focused ion beam having, for example, an accelerating voltage of 30 kV, an ion beam current of 150 pA, and a beam diameter of 0.1 μm, and a cross-section of the wiring area was exposed. Further, the focused ion beam for the semiconductor device (10) was irradiated on the cleaved surface under the same conditions so as to carry out sputter-etching over the sectional area of the wiring. As a result, as show in FIG. 4(e), the area of the Al alloy film (54) was more largely etched than other areas such as the barrier metal (53) and the cap metal (55), and unevenness was formed on the surface of the cross-section of the semiconductor device (10).

Figure 4D:
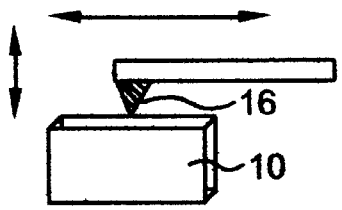

Next, as shown in FIG. 4(d), the cross section of said semiconductor device (10) was scanned with the cantilever (16) using an AFM. Then atomic force between said semiconductor device (10) and the cantilever (16) was measured and the cross-section of said semiconductor device (10) was observed. A SiN needle or SiC needle was used as a probe for the AFM. Measurement by the AFM was carried out while keeping the atomic force (attraction and repulsion) at a constant level.

In the invention, a semiconductor device with a specific pattern was described. But the same effect is obtained from observation of the crystal grains of such an Al alloy film that is made of an Al alloy film having no pattern or a laminated Al alloy film.

Hereinafter, the drawings of the analysis method for the crystal grains of the Al alloy or laminated Al alloy film of the semiconductor devices of the third embodiment of the invention will be described. Used in the third embodiment is the same analysis apparatus as in the first embodiment.

Figure 5A:
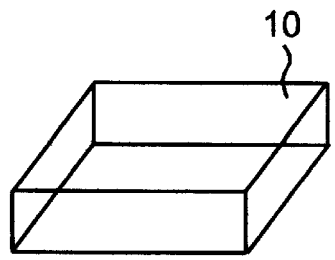
FIGS. 5(a)–5(e) show cut-away views showing steps of the analysis method for semiconductor devices in the third embodiment.

FIGS. 5(a)–(e) show steps of the analysis method for the semiconductor devices of the third embodiment. FIG. 5(a) is a cut-away view of the semiconductor device (10), which has a laminate-structured wiring area.

Figure 5B:
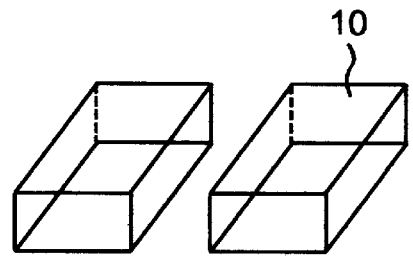

First, like the second embodiment, the semiconductor device (10) was cleaved with a diamond pen or a dicing saw, as shown in FIG. 5(b).

Figure 5C:
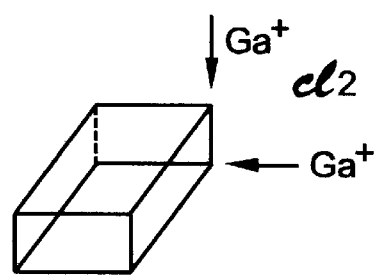

Next, as shown in FIG. 5(c), sputter-etching was carried out over the cleaved surface of said semiconductor device (10) with a positive Ga focused ion beam having an accelerating voltage of 30 kV, an ion beam current of 150 pA, and a beam diameter of 0.1 μm laterally from the side to reduce roughness of the cleaved surface of the semiconductor device (10), and a cross-section of the wiring area was exposed. Then, the focused ion beam was irradiated to the cleaved surface of said semiconductor device (10) at right angles under the same condition. Sputter-etching was also carried out over the sectional area of the wiring. Afterward $Cl_2$ etching gas, for example, was injected from the gas nozzle (9) onto an irradiation area of the focused ion beam and the focused ion beam was irradiated so as to carry out gas-assist etching all over the Al wiring area.

Figure 5E:
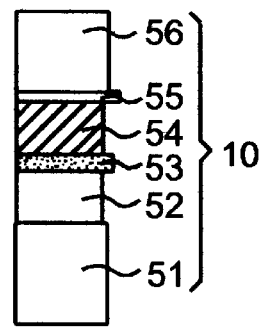

As shown in FIG. 5(e), the area of the Al alloy film (54) was more largely etched than other areas such as the barrier metal (53) and the cap metal (55). Unevenness was formed on the surface of the cross-section of the semiconductor device (10).

Figure 5D:
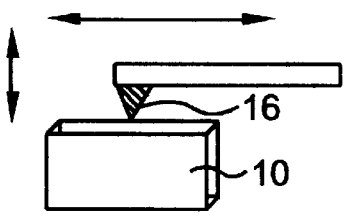

Next, as shown in FIG. 5(d), the cross-section of the semiconductor device (10) was scanned with the cantilever (16) using an AFM. Atomic force between the semiconductor device (10) and the cantilever (16) was measured, and the semiconductor device (10) was observed. A SiN needle or SiC needle was used as a probe for the AFM. While keeping the atomic force (attraction and repulsion) at a constant level, measurement with the AFM was carried out.

In the invention, a semiconductor device with a specific pattern was described. But the same effect is obtained from the observation of crystal grains of the Al alloy film made of an Al alloy film having no pattern or a laminated Al alloy film.

In the above embodiment, $Cl_2$ was used as an etching gas, but the same effect can also be obtained by using $XeF_2$, $I_2$, or ICl.

Hereinunder, the fourth embodiment of the invention will be described with reference to the drawings.

Figure 6:
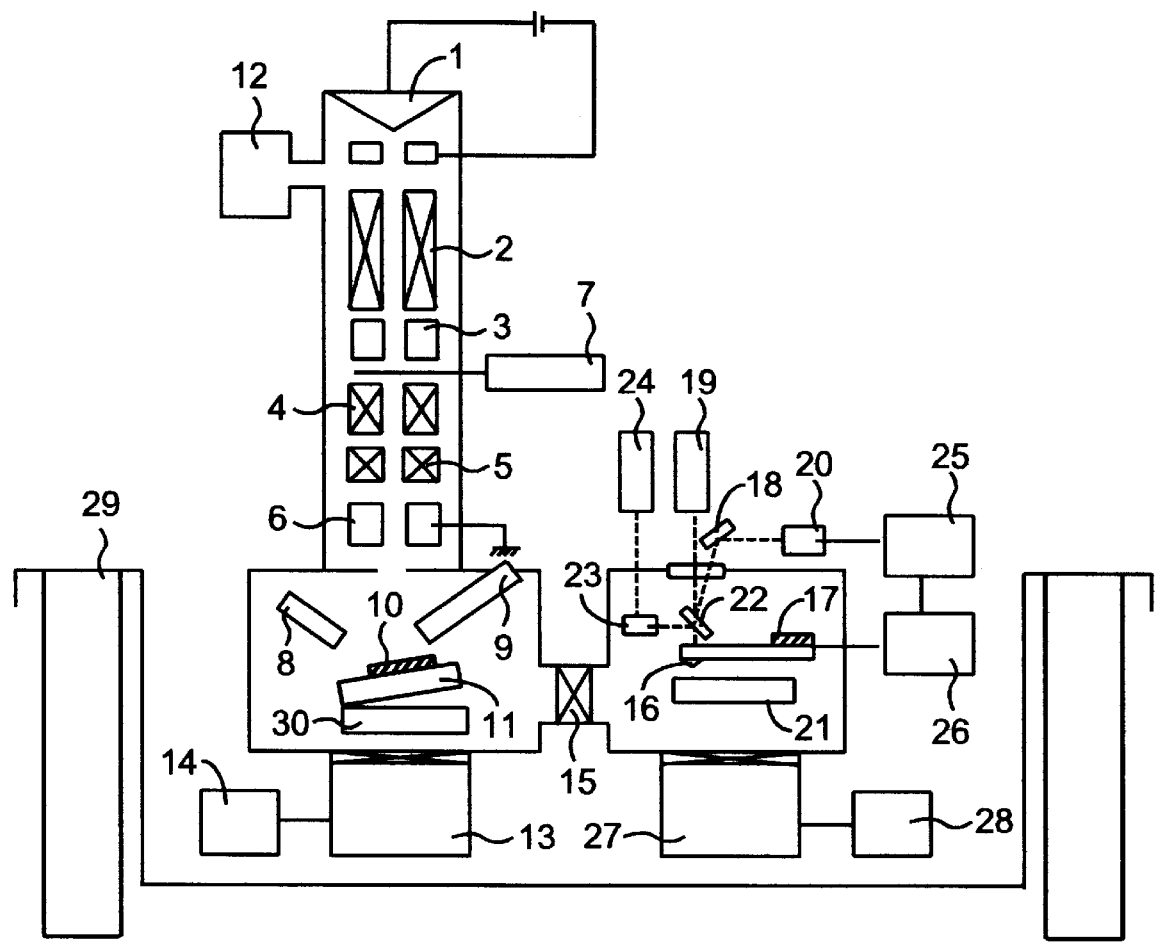
FIG. 6 is a schematic diagram of the analysis apparatus for semiconductor devices used in the fourth through sixth embodiments.

FIG. 6 is a schematic diagram of the analysis apparatus for semiconductor devices of the invention used for the fourth embodiment.

In FIG. 6, reference numerals (1) to (29) represent the same components as for the analysis apparatus for semiconductor devices as described in the first through third embodiments. The only difference of the analysis apparatus of this fourth embodiment from that of the first through third embodiments is that a five axis sample drive unit (30) has been added.

Figure 7:
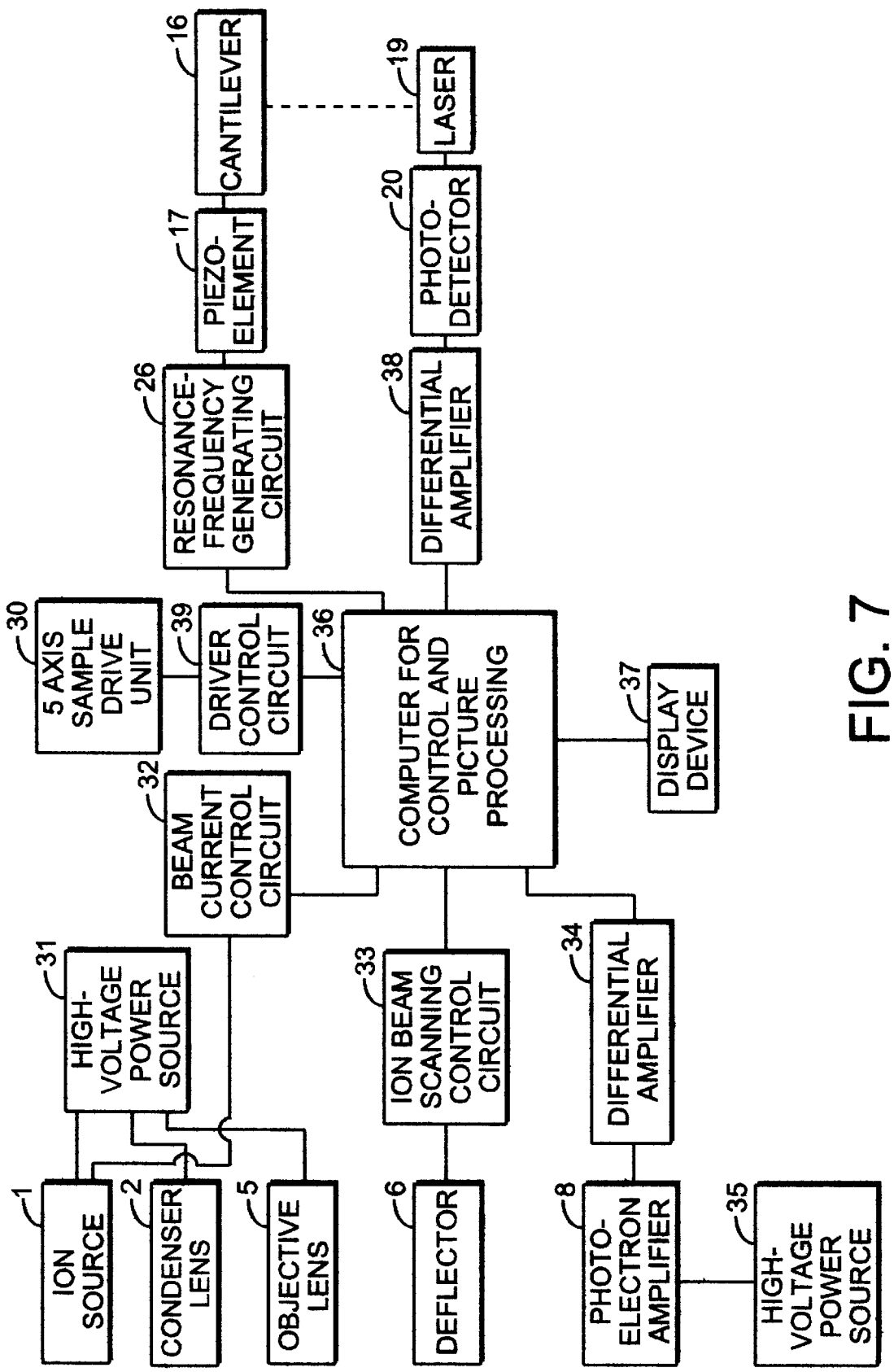
FIG. 7 is a circuit schematic diagram of the analysis apparatus for semiconductor devices used in the fourth through sixth embodiments.

FIG. 7 is a circuit schematic diagram of the analysis apparatus for semiconductor devices.

The different points in this circuit schematic diagram of the fourth embodiment from the analysis apparatus of the first through third embodiments are that the five axis sample drive unit (30) and a driver control circuit (39) have been added.

Next, the analysis method for the crystal grain of the Al alloy film or laminated Al alloy film of the semiconductor devices of the fourth embodiment will be described with reference to the drawings depicting the analysis apparatus.

FIGS. 8(a)–(d) are a cross-sectional views showing the steps of the analysis method for the semiconductor devices of the invention.

Figure 8A:
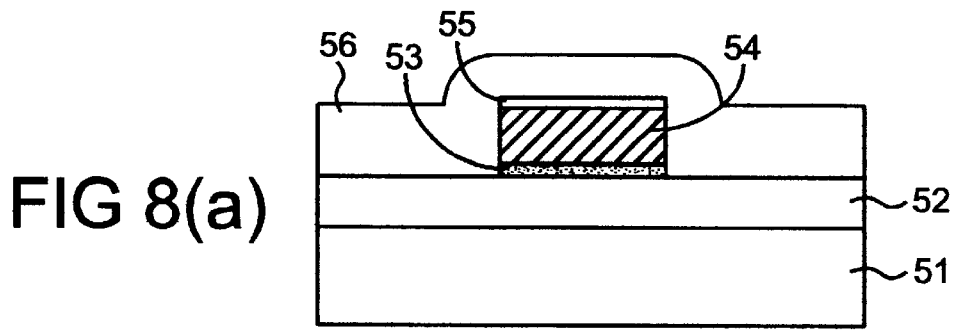
FIGS. 8(a)–8(d) show cross-sectional views showing steps of the analysis method for semiconductor devices in the fourth embodiment.

FIG. 8(a) shows a cross-section of the semiconductor device (10) which has a laminate-structured wiring area like FIG. 3(a).

Figure 8B:
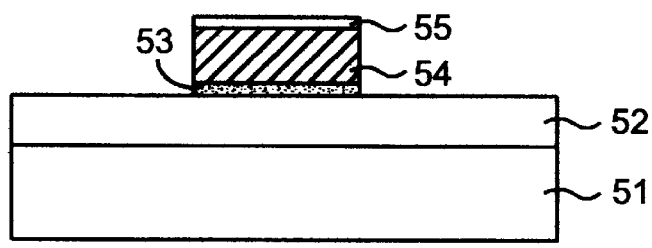

The protective film (56) of the semiconductor device (10) shown in FIG. 8(a) was removed with a dry etching device using a mixed gas made of carbon tetrafluoride gas ($CF_4$) and oxygen to expose the cap metal (55), as shown in FIG. 8(b).

Figure 8C:
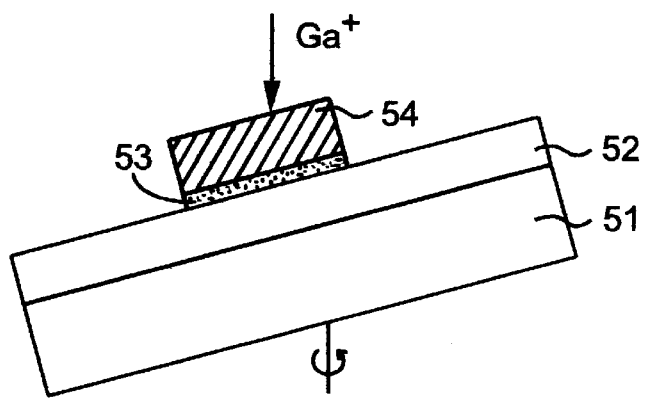

Next, as shown in FIG. 8(c), the semiconductor device (10) was inclined from 15 to 30 degrees, for example 20 degrees, and rotated with the five axis sample drive unit (30). The semiconductor device (10) that was inclined and rotated was scanned with a positive Ga focused ion beam having an accelerating voltage of 30 kV, an ion beam current of 150 pA, and a beam diameter of 0.1 μm. Sputter-etching was carried out over the cap metal (55) to expose the Al alloy film (54). The amount of the sputter-etching was controlled by detecting by means of the photomultiplier (8) secondary electrons generated by scanning the semiconductor device (10) with a focused ion beam. With this sputter-etching, the surface and grain boundary areas of the preferred orientation were selectively etched, and unevenness was formed on the Al surface.

Figure 8D:
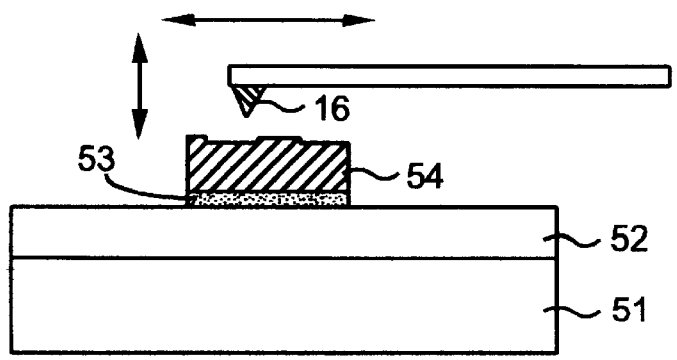

FIG. 8(d) shows the state of unevenness of the cross-section. The amount of etching was large on the Al (111) surface and small on the Al (100) surface and the Al (110) surface. In addition, the amount of etching was large in grain boundary areas.

Next, as shown in FIG. 8(d), the surface of the semiconductor device (10) was scanned with the cantilever (16), using an AFM. Atomic force between the semiconductor device (10) and the cantilever 16 was measured, and the semiconductor device (10) was analyzed.

A SiN needle or SiC needle was used as a probe for the AFM. Measurement by the AFM was carried out in vacuum while keeping the atomic force (attraction or repulsion) at a constant level.

In general, sputtering yields of polycrystal bodies by ion beams greatly depend on the azimuth of the surface of the crystal grain, the channeling effect, the grain boundary, and precipitated material. Therefore, unevenness information provided by the AFM is influenced by the difference of crystal azimuth, grain boundary, and precipitated material. In the invention, since the sample is inclined and rotated from 15 to 30 degrees while being scanned with a focused ion beam, the probability of collision between the ion beams and atoms constituting each crystal surface is increased, and the channeling effect of sputtering yields of polycrystal bodies can be inhibited. Thus, crystal grains can be observed by using an AFM and images with high resolutions can be obtained. Further, the azimuth of the crystal surface can be identified from the unevenness information from the AFM and a structural analysis of the Al alloy film can be carried out.

In the invention, the semiconductor device with a specific pattern was described, but the same effect can be obtained with respect to the observations and structural analyses of the crystal grains of the Al alloy film made of an Al alloy film having no pattern or a laminated Al alloy film.

Now, with reference to further drawings, the observation and structural analysis method for crystal grains of the Al alloy film or laminated Al alloy film of the semiconductor devices of the fifth embodiment of the invention will be described. The analysis method of the fifth embodiment used the same analysis apparatus as in the fourth embodiment. FIGS. 9(a)–(f) are a schematic diagrams showing the analysis method for the semiconductor devices of the fifth embodiment.

Figure 9A:
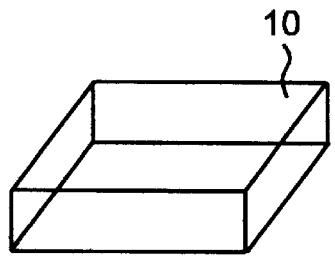
FIGS. 9(a)–9(f) show cut-away views showing steps of the analysis method for semiconductor devices in the fifth embodiment.
Figure 9B:
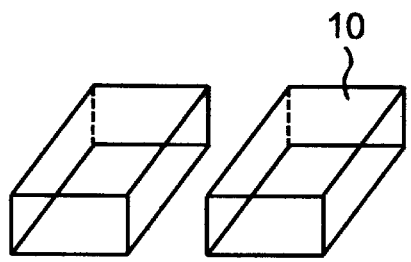

Like the first through fourth embodiments, the semiconductor device (10) which had a laminate-structured wiring area as shown in FIG. 9(a) was cleaved with a diamond pen or a dicing saw, as shown in FIG. 9(b).

Figure 9C:
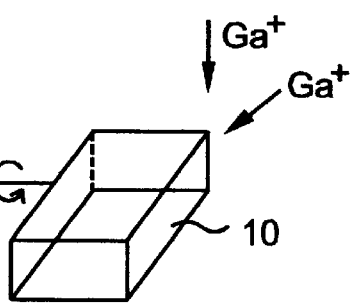
Figure 9D:
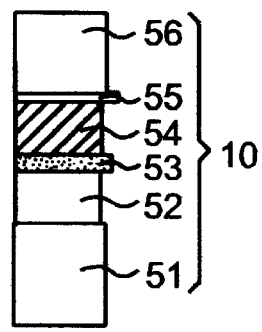

Next, sputter-etching was carried out over the cleaved surface of the semiconductor device (10) laterally from the side with a positive Ga focused ion beam having an accelerating voltage of 30 kV, an ion beam current of 150 pA, and a beam diameter of 0.1 μm to reduce the roughness of the cleaved surface of the semiconductor device (10) as shown in FIG. 9(c). Then a cross-section of the wiring area was made. Next, the semiconductor device (10) was inclined at an angle of 15 to 20 degrees and rotated with a five axis sample drive unit. While rotating, a focused ion beam is irradiated slantedly onto the cleaved surface of the semiconductor device (10) under the same condition, and sputter-etching was carried out over the sectional area of the wiring. As a result, as show in FIG. 9(d), the area of the Al alloy film (54) was more largely etched than other areas such as the barrier metal (53) and the cap metal (55), and unevenness was formed on the cross section of the semiconductor device (10).

Figure 9E:
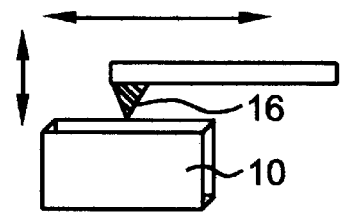
Figure 9F:
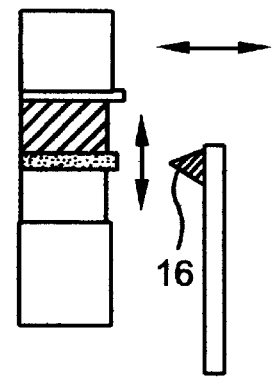

Next, as shown in FIGS. 9(e) and (f), the surface of the semiconductor device (10) was scanned with the cantilever (16), using an AFM. The atomic force between the semiconductor device (10) and the cantilever (16) was measured and the cross-section of the semiconductor device (10) was observed. A SiN needle or SiC needle was used as a probe for the AFM. Measurement with the AFM was carried out in vacuum while keeping the atomic force (attraction or repulsion) at a constant level.

In the invention, the semiconductor device with a specific pattern was described. But the same effect can be obtained with respect to the observation and structural analysis of the crystal grains of the Al alloy film made of an Al alloy film having no pattern or a laminated Al alloy film.

Lastly, with reference to FIGS. 10(a)–(f), the observation and structural analysis method for the crystal grain of the Al alloy film or laminated Al alloy film of the semiconductor devices of the sixth embodiment will be described. The same analysis apparatus as in the fourth embodiment is used for the analysis method of the sixth embodiment.

FIGS. 10(a)–(f) are a schematic diagram showing the analysis method for the semiconductor devices of the embodiment.

Figure 10A:
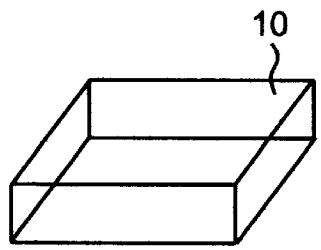
FIGS. 10(a)–10(f) show cut-away views showing steps of the analysis method for semiconductor devices of the sixth embodiment.

FIG. 10(a) shows the semiconductor device (10) with a wiring area having a laminated structure.

Figure 10B:
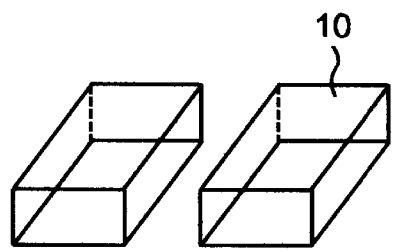

Like the fifth embodiment, the semiconductor device (10) was cleaved with a diamond pen or a dicing saw, as shown in FIG. 10(b).

Figure 10C:
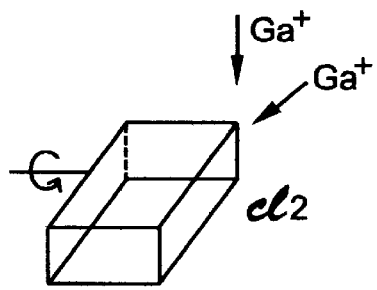

Next, as shown in FIG. 10(c), in order to reduce the roughness of the cleaved surface of the semiconductor device (10), the cleaved surface was scanned in parallel thereto with a positive Ga focused ion beam having, for example, an accelerating voltage of 30 kV, an ion beam current of 150 pA, and a beam diameter of 0.1 µm, thereby carrying out sputter-etching over the semiconductor device (10), and making a cross-section of the wiring area. Then, the semiconductor device (10) was inclined at an angle of 15 to 20 degrees and rotated with a five axis sample drive unit. While rotating the semiconductor device (10), the focused ion beam was irradiated slantedly onto the cleaved surface of the semiconductor device (10). Then, an etching gas such as $Cl_2$ gas was introduced through the gas nozzle 9 onto the irradiation area of the focused ion beam and the focused ion beam was irradiated slantedly onto the area, thereby carrying out gas-assist etching over the Al wiring area.

Figure 10D:
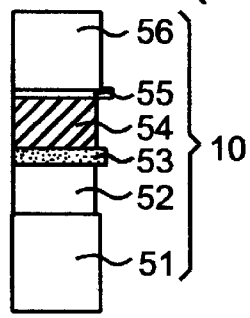

As shown in FIGS. 10(d) and (f), the area of the Al alloy film (54) was more largely etched than other areas such as the barrier metal (53) and the cap metal (55), and unevenness was formed on the surface of the cross-section of the semiconductor device (10).

Figure 10E:
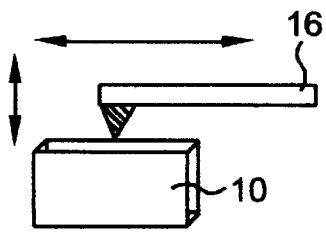
Figure 10F:
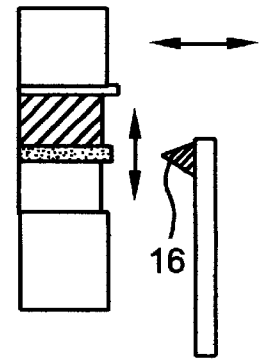

Next, as shown in FIG. 10(e), the surface of the cross section of the semiconductor device (10) was scanned with the cantilever (16), using AFM. Atomic force between the semiconductor device (10) and the cantilever (16) was measured, and the semiconductor device (10) was observed. A SiN needle or SiC needle was used as a probe for the AFM. Measurement with the AFM was carried out in vacuum while keeping the atomic force (attraction and repulsion) at a constant level.

Although the semiconductor device with a specific pattern has been referred to and described in the invention, the same effect can be obtained with respect to the observation and structural analysis of the crystal grains of such an Al alloy film as made of an Al alloy film having no pattern or a laminated Al alloy film.

According to the description in the fourth through sixth embodiments, $Cl_2$ was used as the etching gas, but the same effect can be obtained when $XeF_2$, $I_2$ or ICl is used instead.

What is claimed is:

1. An analysis method for semiconductor devices, comprising the steps of:

removing a protective film from a semiconductor device by dry etching;

inclining said semiconductor device to an angle in the range of about 15–30 degrees;

rotating said inclined semiconductor device;

scanning an aluminum containing film of said inclined and rotating semiconductor device with a focused ion beam; and scanning said aluminum film with a cantilever, measuring atomic force between said aluminum film and the cantilever, and observing the surface of said aluminum film in vacuum.

2. An analysis method for semiconductor devices, comprising the steps of:

cleaving a semiconductor device;

inclining said semiconductor device to an angle in the range of about 15–30 degrees;

rotating said inclined semiconductor device;

etching the cleaved local areas of said inclined and rotating device by scanning the areas with a focused ion beam; and scanning the local areas of said semiconductor device with a cantilever, measuring atomic force between said semiconductor device and the cantilever, and observing the surface of an aluminum containing film of said semiconductor device in vacuum.

3. The analysis method for semiconductor devices according to claim 2, comprising the additional step of etching the cleaved local areas of this semiconductor device by scanning the areas with a focused ion beam in an etching gas atmospheres, after said step of etching the cleaved local areas of said semiconductor device by scanning the areas with the focused ion beam.

4. An analysis method for semiconductor devices according to claim 1, wherein the accelerating voltage of the focused ion beam is within the range of 20 to 30 kv.

5. An analysis method for semiconductor devices according to claim 2, wherein said step of etching the cleaved local areas comprises etching the cleave surface of said semiconductor device by scanning the areas with a focused ion bean in parallel to the cleaved surface and in a perpendicular direction to said semiconductor device, wherein said step of etching the cleaved surface further comprises scanning the areas with a focused ion beam in a perpendicular direction to the cleaved surface.

6. An analysis method for semiconductor devices according to claim 3, wherein $Cl_2$, $XeF_2$, $I_2$ or ICl is used as the etching gas.

7. The analysis method for semiconductor devices according to claim 1, wherein said aluminum containing film is made from a material selected from the group consisting of aluminum and an aluminum alloy.

8. The analysis method for semiconductor devices according to claim 1, wherein said aluminum containing film is laminated.

9. The analysis method for semiconductor devices according to claim 2, wherein said aluminum containing film is made from a material selected from the group consisting of aluminum and an aluminum alloy.

10. The analysis method for semiconductor devices according to claim 2, wherein said aluminum containing film is laminated.

11. The analysis method for semiconductor devices according to claim 2, wherein the accelerating voltage of the focused ion beam is within the range of 20 to 30 kv.

\* \* \* \* \*